United States Patent
Cigler et al.

(10) Patent No.: US 11,744,855 B2
(45) Date of Patent: Sep. 5, 2023

(54) NANODIAMONDS AS ARTIFICIAL PROTEINS FOR REGULATION OF A CELL SIGNALLING SYSTEM

(71) Applicants: USTAV ORGANICKE CHEMIE A BIOCHEMIE AV CR, V.V.I., Prague (CZ); MASARYKOVA UNIVERZITA, Brno (CZ); FAKULTNI NEMOCNICE U SV. ANNY V BRNE, Brno (CZ)

(72) Inventors: Petr Cigler, Prague (CZ); Lukas Balek, Klimkovice (CZ); Jan Havlik, Znojmo (CZ); Pavel Krejci, Brno (CZ); Lukas Trantirek, Brno (CZ); Silvie Trantirkova, Brno (CZ)

(73) Assignees: USTAV ORGANICKE CHEMIE A BIOCHEMIE AV CR, V.V.I, Prague (CZ); MASARYKOVA UNIVERZITA, Brno (CZ); FAKULTNI NEMOCNICE U SV, ANNY V BRNE, Brno (CZ)

( * ) Notice: Subject to any disclaimer, the term of this patent is extended or adjusted under 35 U.S.C. 154(b) by 63 days.

(21) Appl. No.: 16/981,578

(22) PCT Filed: Mar. 26, 2019

(86) PCT No.: PCT/EP2019/057649
§ 371 (c)(1),
(2) Date: Sep. 16, 2020

(87) PCT Pub. No.: WO2019/185667
PCT Pub. Date: Oct. 3, 2019

(65) Prior Publication Data
US 2021/0015856 A1 Jan. 21, 2021

(30) Foreign Application Priority Data
Mar. 30, 2018 (EP) .................... 18165299

(51) Int. Cl.
A61K 33/44 (2006.01)
A61K 9/14 (2006.01)
A61K 45/06 (2006.01)
C07K 14/50 (2006.01)

(52) U.S. Cl.
CPC ............ *A61K 33/44* (2013.01); *A61K 9/14* (2013.01); *A61K 45/06* (2013.01); *C07K 14/50* (2013.01)

(58) Field of Classification Search
CPC .................................. C07K 14/50
See application file for complete search history.

(56) References Cited

U.S. PATENT DOCUMENTS

2015/0182624 A1* 7/2015 Petit ................ A61K 41/00

FOREIGN PATENT DOCUMENTS

WO 2014191633 A2 12/2014

OTHER PUBLICATIONS

Harriet R. Ferguson, Fibroblast Growth Factor Receptors (FGFRs) and Noncanonical Partners in Cancer Signaling, Cells 2021, 10, 1201 (Year: 2021).*
Xin Wang et al, Epirubicin-Adsorbed Nanodiamonds Kill Chemoresistant Hepatic Cancer Stem Cells, ACS AuthorChoice, vol. 8, No. 12, 12151-12166, 2014 (Year: 2014).*
Dynamic Biosensors, How is the Hydrodynamic Diameter defined?, Dynamic Biosensors GmbH (HQ) Germany, downloaded in Jan. 2022 (Year: 2022).*
Dean Ho et al, Nanodiamonds: The intersection of nanotechnology, drug development, and personalized medicine, Sci. Adv. 2015; 1:e1500439 (Year: 2015).*
Marta Grodzik et al, Nanoparticles of carbon allotropes inhibit glioblastoma multiforme angiogenesis in ovo, International Journal of Nanomedicine 2011:6 3041-3048 (Year: 2011).*
Mary Elizabeth Davis, Glioblastoma: Overview of Disease and Treatment, Clin J Oncol Nurs. Oct. 1, 2016; 20(5): S2-S8 (Year: 2016).*
Moore et al: Multi-protein Delivery by Nanodiamonds Promotes Bone Formation, Journal of Dental Research, vol. 92, No. 11, Sep. 17, 2013 (Sep. 17, 2013), pp. 976-981, XP055478721, ISSN: 0022-0345, abstract.
Mateusz Wierzbicki et al: "Comparison of anti-angiogenic properties of pristine carbon nanoparticles", Nanoscale Research Letters, Dec. 1, 2013 (Dec. 1, 2013), pp. 1-8, XP055478747, New York DOI: 10.1186/1556-276X-8-195 Retrieved from the Internet: URL:https://nanoscalereslett.springeropen. com/track/pdf/10.1186/1556-276X-8-195, downloaded Sep. 15, 2020.
Andre Chwalibog et al: "Carbon nanoparticles downregulate expression of basic fibroblast growth factor in the heart during embryogenesis", International Journal of Nanomedicine, Sep. 1, 2013 (Sep. 1, 2013), p. 3427, XP055478735, DOI: 10.2147/IJN.S49745.
International Search Report and Written Opinion for corresponding PCT application No. PCT/EP2019/057649, dated May 17, 2019.

* cited by examiner

Primary Examiner — Mark V Stevens
Assistant Examiner — Alparslan Asan
(74) Attorney, Agent, or Firm — Notaro, Michalos & Zaccaria P.C.

(57) ABSTRACT

Nanodiamonds having a positive ζ-potential of at least 1 mV for use in sequestration of at least one FGF family member in organisms in vivo and in vitro. It has been found that nanodiamonds with a positive ζ-potential show an extremely strong and selective binding to FGF family members, thus leading to their usability in the treatment of diseases related to aberrant FGF-FGFR signalling and/or interaction.

9 Claims, 6 Drawing Sheets

Fig. 7

NANODIAMONDS AS ARTIFICIAL PROTEINS FOR REGULATION OF A CELL SIGNALLING SYSTEM

FIELD OF ART

The present invention relates to nanodiamonds and their use in FGF family members sequestration.

BACKGROUND ART

Fibroblast growth factors (FGFs) are multifunctional proteins involved in cell proliferation, differentiation, regeneration and metabolism in mammals. The FGF system represents a major molecular system by which cells sense their extracellular environment and respond to communication signals during development, life and disease. Four human FGF-receptors exist (FGFR1-4) which respond to communication signals delivered by at least 18 FGF ligands. The importance of FGFR signaling is further emphasized by evidence of their pathological functions. Many pathological conditions arise from aberrant FGF/FGFR signaling, including cancers, developmental defects and metabolic disorders [Ornitz, D. M. and Marie, P. J., *Genes Dev.* 2015, 29, 1463; Wesche, J. et al., *Biochem. J.* 2011, 437, 199].

Inhibition of FGF signaling leads to inhibition of proliferation and induction of apoptosis, particularly during tumor suppression. FGFR inhibitors further enhance tumor sensitivity to conventional chemotherapy such as 5-fluorouracil, irinotecan, paclitaxel and etoposide (*Cancer Lett.* 2011 Aug. 1; 307(1):47-52; *Int J Cancer.* 2010 Feb. 15; 126(4):1004-16). A number of FGFR inhibitors are currently in clinical trials, however, they are often non-selective and show inhibition of other growth factor signaling which results in undesired side effects.

Various FGFR inhibitors are tested against diseases caused by aberrant FGF-FGFR signalling and/or interaction (caused by overproduction of one or more FGF ligands, or activation of mutated and/or unregulated FGFRs with physiological levels of FGFs) such as breast cancer, multiple myeloma, renal cell carcinoma, metastatic renal cell carcinoma, urothelial carcinoma, bladder cancer, endometrial cancer, lung and lymph node metastasis, melanoma, biliary cancer, gastric and gastro-oesophageal cancer, glioma, squamous cell carcinoma, cholangiocarcinoma. They have been observed to cause a number of undesired side effects, likely also due to their non-selectivity or limited selectivity (*Oncotarget* 2017 Feb. 28; 8(9): 16052-16074).

In developing bone, FGF signaling inhibits chondrocyte proliferation and has a critical role in skeletal development which results in severe growth aberrations such as dwarfism and impaired bone regeneration in injuries when the FGF signaling is dysregulated, or FGF is overproduced, respectively.

Since the upswing of nanomedicine in the early 1990s, the use of nanoparticles has strongly influenced the quality of treatment of various diseases and pathogens. The low toxicity of some nanoparticles, their high surface to volume ratio and the possibility of polyvalent binding sites on their surface have enabled the application of nanoparticles in targeted drug delivery systems, of theranostic nanoparticles that perform simultaneous therapeutic intervention and monitoring of the treatment, and of stimulus-responsive systems based on hybrid nanoparticles with a broad structural range. Overcoming some of the current barriers in cancer treatment, such as poor circulation times, drug resistance and off-target toxicity, using nanotechnology-based systems catalysed the development of a number of drug delivery nanosystems that have already passed the translation phases and are currently marketed as drugs.

More recently, promising new directions utilizing nanoparticles for the selective binding or sequestration of biologically active and regulatory compounds have also been investigated. However, owing to issues such as the lack of well-defined binding pockets, developing nanoparticles that selectively modulate protein-protein interactions remains highly challenging. Moreover, the nanoparticles used for the selective control of protein-protein interactions have always been decorated with a bionanointerface consisting of (bio) organic molecules and/or polymers. The organic functional groups presented on nanoparticles and their flexible arrangement, however, can cause unwanted interactions, for example with immune cells [Dobrovolskaia, M. A. et al., *Molecular Pharmaceutics* 2008, 5, 487].

L. Moore et al., in *J. Dent. Res.* 2013, 92, 976, disclose the use of FGF as a healing substance for treatment of local disorders caused by lack of FGF, for example, FGF2 can be delivered in combination with bone morphogenetic protein 2 (BMP-2) as a mixed complex with nanodiamonds. Simultaneous delivery of BMP-2 and FGF2 by nanodiamonds induces differentiation and proliferation in osteoblast progenitor cells.

DISCLOSURE OF THE INVENTION

The present invention is based on the finding that nano-sized diamond crystals (nanodiamonds, NDs) show an extremely strong and selective binding of members of the fibroblast growth factor (FGF) family in complex biological systems. However, it was found that in order to show these properties, the nanodiamonds must have a positive ξ-potential. The said binding to the members of the FGF family is sufficiently strong and selective to selectively sequester the FGF family members even from complex mixtures of proteins, i.e., from biological systems.

The selective binding of FGF family members to nanodiamonds can effectively sequester FGFs at their biologically relevant concentrations, compete with their interaction with FGFR and mitigate their biological effects in a concentration-dependent manner. This regulation of protein-protein interaction is effective in a biological environment containing other proteins than FGF. The regulation is also highly selective: minimal influence on other signalling systems unrelated to FGF, such as TGFβ, IL6, IFNγ, EGF and NGF was observed. This quality of the interaction is similar to that of the highly potent biomolecular interactions evolved in nature. Finally, thanks to the extremely tight FGF-ND binding, even highly diluted nanodiamond colloids are able to mitigate aberrant FGF signalling and/or interaction and promote the restoration of cartilage growth in the mouse limb explant model. Notably, no manifestations of nanodiamond toxicity were observed in a broad range of tested concentrations.

The present invention thus provides the nanodiamonds for use in the treatment of diseases caused by aberrant FGF-FGFR signalling and/or aberrant FGF-FGFR interaction without the risks of undesired side effects, thanks to the strength of the interaction allowing the use of low concentrations, and thanks to the selectivity of the interactions, thus preventing the side effects arising from interaction with other proteins and components of biological systems.

"Aberrant FGF-FGFR signalling" refers herein to the aberrant signaling caused by overproduction of one or more FGF ligands, or activation of mutated and/or unregulated FGFRs with physiological level of FGFs. Diseases (e.g., conditions and disorders) caused by this aberrant FGF-FGFR signalling can be treated or improved by sequestration of the FGF ligands, i.e., FGF family members.

"Aberrant FGF-FGFR interaction" refers herein to diseases (e.g., conditions and disorders) caused by physiological levels of FGFs acting on mutated FGFRs, in particular by physiological levels of FGFs activating mutated FGFRs, such as craniosynostoses or skeletal dysplasias such as achondroplasia caused by activating mutations in FGFR1, FGFR2 and FGFR3.

The present invention also provides a method of treatment of a disease caused by aberrant FGF-FGFR signalling and/or aberrant FGF-FGFR interaction, comprising the step of administration of nanodiamonds having a positive ξ-potential of at least 1 mV to a subject in need of such treatment.

Further, the nanodiamonds can also be used in vitro in sequestration of FGF family members from biological mixtures such as tissues or cell cultures.

The present invention provides nanodiamonds having a positive ξ-potential of at least 1 mV for use in sequestration of one or more FGF family members in organisms in vivo.

In particular, the nanodiamonds having a positive ξ-potential of at least 1 mV for use in the treatment of a disease caused by aberrant FGF-FGFR signalling and/or interaction.

The diseases caused by aberrant FGF-FGFR signalling and/or interaction preferably include cancers, developmental defects and metabolic disorders. More preferably, the diseases caused by the aberrant FGF-FGFR signalling and/or interaction are selected from breast cancer, multiple myeloma, renal cell carcinoma, metastatic renal cell carcinoma, urothelial carcinoma, bladder cancer, endometrial cancer, lung and lymph node metastasis, melanoma, biliary cancer, gastric and gastro-oesophageal cancer, glioma, glioblastoma, squamous cell carcinoma, cholangiocarcinoma, craniosynostoses, skeletal dysplasias, dwarfism and impaired bone growth or regeneration.

In one embodiment, the nanodiamonds having a positive ξ-potential of at least 1 mV are provided for use in the treatment of a disease caused by aberrant FGF-FGFR signalling and/or interaction which is a cancer, wherein a second agent is administered, said second agent being an anticancer drug such as 5-fluorouracil, irinotecan, paclitaxel or etoposide.

A method of treatment of a disease caused by aberrant FGF-FGFR interaction and/or signalling is also provided, comprising the step of administering nanodiamonds to the subject in need of such treatment. In one embodiment, a second agent is administered, said second agent being an anticancer drug such as 5-fluorouracil, irinotecan, paclitaxel or etoposide.

The present invention further provides the use in vitro of the nanodiamonds having a positive ξ-potential of at least 1 mV in sequestration of one or more FGF family members from biological mixtures such as tissues, cell cultures and/or protein-containing mixtures.

The nanodiamonds for use in the present invention must show a positive ξ-potential of at least 1 mV, preferably at least 20 mV and more preferably at least 40 mV. It was observed that nanodiamonds with negative ξ-potential do not bind strongly and selectively to FGF family members.

The nanodiamonds preferably have an average diameter of primary particles in the range of 1 to 10 nm, as measured using transmission electron microscopy.

The nanodiamonds typically form aqueous colloidal solutions containing nanoparticles which preferably have a hydrodynamic diameter, determined as peak maximum size using dynamic light scattering, within the range of 1-100 nm, preferably 1-70 nm, more preferably 3-50 nm.

The nanodiamonds are preferably detonation nanodiamonds (ultradispersed detonation nanodiamonds). Detonation nanodiamonds are nanodiamonds originating from a detonation. Typically, an oxygen-deficient explosive mixture of trinitrotoluene and RDX (1,3,5-trinitro-1,3,5-triazinane) is detonated in a closed reactor and at the front of the detonation wave, nanodiamond particles are formed. The detonation nanodiamonds typically have the dimensions preferred for this invention.

FGF family members (or FGF ligands) include 18 members of the FGF family, divided into several subfamilies. The FGF1 subfamily includes FGF1 and FGF2. The FGF4 subfamily includes FGF4, FGF5 and FGF6. The FGF7 subfamily includes FGF3, FGF7, FGF10 and FGF22. The FGF9 subfamily includes FGF9, FGF16, FGF20. The FGF8 subfamily includes FGF8, FGF17 and FGF18. The FGF19 subfamily includes FGF19, FGF21 and FGF-23.

More preferably, the FGF family members are selected from FGF1, FGF2, FGF4, FGF7, FGF8, FGF9, FGF10, FGF17, FGF18, FGF19, FGF21, FGF22, FGF23.

The present invention is further illustrated by the following examples which should not be construed as limiting the scope of the claims.

LIST OF ABBREVIATIONS USED IN THE DRAWINGS AND EXAMPLES

DMEM—Dulbecco's modified Eagle media
EGF—epidermal growth factor
ERK—extracellular signal-regulated kinase
E18—embryonal day 18
FBS—fetal bovine serum
FGF—fibroblast growth factor
FGFR—fibroblast growth factor receptor
FRS2—fibroblast growth factor receptor substrate 2
IL6—interleukin 6
IFNγ—interferon γ
LRP6—low density lipoprotein 6
MCF7—Michigan Cancer Foundation-7 cells
ND—nanodiamonds
ND-HPHT—high-pressure, high-temperature nanodiamonds
ND-PL—detonation nanodiamonds with negative ξ-potential
ND1, ND2—detonation nanodiamonds with positive ξ-potential
NGF—nerve growth factor
QELS—quasielastic light scattering
PVDF—polyvinyl difluoride
RCS—rat chondrosarcoma cells
SD—standard deviation
SDS-PAGE—polyacrylamide gel electrophoresis in the presence of sodium dodecylsuphate
STAT1, STAT3—signal transducer and activator of transcription 1 and 3
SMAD2—mothers against decapentaplegic homolog 2 transcription factor
TGFβ—transforming growth factor β
TRKA—receptor tyrosine kinase TRKA
WNT—morphogene from the WNT family

BRIEF DESCRIPTION OF DRAWINGS

FIGS. 4A-4C NDs inhibit the FGF2-mediated activation of FGFR signalling and the induction of senescence. (A) RCS cells were treated in medium containing 10% FBS with 20 ng/ml FGF2, 10 μg/ml ND2, and 10 nM BGJ398. The effects of inhibitors on the FGF2-mediated induction of the senescence markers lamin A/C and caveolin was determined by western blot 72 hours later. The reduction in ID2 expression, which correlates with premature senescence in RCS cells, is also shown. Actin served as a loading control; n, number of independent experiments. (B) Cells were treated with FGF2 and ND1 for the indicated times, and the ND effect on the FGF2-mediated phosphorylation (p) of LRP6, FRS2 and ERK members of FGFR downstream signalling pathways was determined by western blot. The total levels of each molecule and actin serve as loading controls. (C) 293T cells were transfected with vectors expressing wild-type (WT) FGFR3 and its activating mutant K650M, and treated with ND2 for 24 hours. Cells were analysed for indicated molecules by WB. Note the phosphorylation (p) of K650M-FGFR3 and ERK which is not counteracted by ND2. Similarly, ND2 does not interfere with activation of ERK by WT FGFR3.

FIGS. 5A-5D NDs inhibit FGF signalling but not TGFβ1, IL6, IFNγ, EGF or NGF signalling. (A) RCS or (B) MCF7 cells were treated in medium containing 10% FBS with 20 ng/ml FGF2, FGF7, FGF9, FGF18 and with 10 ng/ml FGF10 or FGF22 either alone or together with 10 or 15 μg/ml ND2 for 1 hour, and ERK phosphorylation (p) was analysed by western blot. The total ERK levels serve as a loading control; n, number of independent experiments. (C) RCS cells were treated with 20 ng/ml TGFβ1, 50 ng/ml IL6 or 50 ng/ml IFNγ for 10 minutes and analysed for the phosphorylation (p) of SMAD2, STAT1 and STAT3 by western blot. (D) 293T cells were treated with 20 or 50 ng/ml EGF alone or together with NDs for 5 minutes, transfected with vector expressing human wild-type TRKA for 24 hours, and treated with 20 ng/ml NGF alone or in the presence of ND2 for 1 hour. Cells were analysed for ERK phosphorylation (p) with the total ERK serving as a loading control.

FIGS. 6A-6D NDs sequester multiple FGF ligands. Human recombinant FGFs were incubated with NDs in DMEM supplemented with 10% FBS for 8 hours, and the NDs were then collected by centrifugation (100,000 rfc, 2 h). Supernatant and pellet samples were analysed for the presence of FGF by western blot with specific antibodies. The input samples and samples taken after 8-hour incubation but before centrifugation serve as controls. (A) Effective depletion of FGF2 from culture medium by dialyzed ND1. Note the lack of FGF2 signal in the medium supernatant after incubation with ND1. No growth arrest was detected in RCS cells grown in the latter medium supernatant for 72 h, in contrast to the media supernatant containing FGF2 only, which caused normal growth arrest (B). (C) Depletion of soluble recombinant FGF1, FGF4, FGF8, FGF10, FGF17, and FGF22 by ND1 in DMEM supplemented with 10% FBS. The depletion is demonstrated by the lack of FGF signals in the supernatant fraction in the medium containing ND1. (D) No significant depletion of recombinant IL6, IFNγ and IL113 by ND2. IL6, IFNγ and IL113 were detected by western blot with specific antibodies.

EXAMPLES OF CARRYING OUT THE INVENTION

General Materials and Methods

Dispersion of detonation NDs in water, designated as ND1 (NanoAmando), having a positive ξ-potential 56 mV and hydrodynamic diameter 28 nm was supplied by the Nanocarbon Research Institute (Japan).

A sample of oxidized detonation NDs with negative ξ-potential −35 mV and hydrodynamic diameter 79 nm, designated as ND-PL, was obtained from Plasmachem, Germany.

All types of used detonation NDs had an average diameter of primary particles within the range of 1 to 10 nm.

HPHT ND (high-pressure high-temperature nanodiamonds) with negative ξ-potential −48 mV and hydrodynamic diameter 7 nm was supplied by Microdiamant (Switzerland), catalogue number MSY 0-0.05.

For sonication of samples, a Cole Parmer 750 W probe sonicator was used.

Quasielastic light scattering (QELS) and ξ-potential measurements were performed with 1 mg/ml NDs in water using the Zetasizer Nano ZS system (Malvern) at room temperature according to the guidelines of manufacturer.

FGF1, FGF2, FGF4, FGF7, FGF8, FGF9, FGF10, FGF17, FGF18, FGF19, FGF21, FGF22, FGF23, EGF, NGF, TGFβ1, IL1β, IL6, and IFNγ were obtained from RnD Systems (Minneapolis, Minn.); BGJ398 was obtained from Selleckchem (Houston, Tex.).

The following antibodies were used: lamin A/C, ID2, caveolin, LRP6, pFRS2, ERK1/2, pERK1/2, actin, pSTAT1, STAT1, pSTAT3, STAT3, SMAD2, and pSMAD2 (Cell Signaling); FRS2 (Santa Cruz Biotechnology, Santa Cruz, Calif.); pLRP6 (Millipore, Billerica, Mass.); V5 (Invitrogen); FGF2 (Sigma-Aldrich); and FGF1, FGF4, FGF8, FGF10, FGF17, FGF19, FGF21, FGF22, FGF23, IL1β, IL6, and IFNγ (RnD Systems).

Example 1

Preparation of Nanodiamond (ND) Colloids:

ND1: The dispersion of detonation ND purchased from NanoAmando (10 ml, 5.0%) was diluted with water to a concentration of 10 mg/ml, sonicated for 10 min and filtered using a 0.2 μm PVDF syringe filter.

ND2: ND1 colloidal solution (40 ml, 10.3 mg/ml) was centrifuged in an ultracentrifuge Beckman Coulter Le80K with an SW 41 Ti swinging bucket rotor (15,000 rfc, 2 h).

The supernatant was isolated and filtered using a 0.2 μm PVDF syringe filter, yielding ND2 colloid (26 ml, 7.8 mg/ml) with positive ξ-potential 49 mV and hydrodynamic diameter 21 nm.

ND-PL: The ND powder (3 mg) was mixed with 3 ml of water in a plastic tube and sonicated for 60 min using a probe sonicator in an ice bath. The obtained colloid was filtered using a 0.45 μm glass microfibre syringe filter.

HPHT NDs were oxidized by air in a Thermolyne 21100 tube furnace at 510° C. for 5 hours. The NDs were subsequently treated with a mixture of $HNO_3$ and $H_2SO_4$ (90° C., 3 days), with 1 M NaOH (80° C., 1 h) and finally with 1 M HCl (80° C., 1 h). Between treatments, the NDs were separated by centrifugation at 5000 rcf (relative centrifugal force) (20 min). After HCl treatment, the diamonds were 3× centrifuged (5000 rcf, 20 min; 7000 rcf, 30 min; 20,000 rcf, 30 min) and redispersed using a tip sonicator. The brown colloid remaining after the last centrifugation was diluted with water to yield a solution of ND-HPHT (1 mg/ml).

Determination of ND Concentration:

The analysed sample (1000 μl) was evaporated in a pre-weighted 1.5 ml Eppendorf tube using a Labconco Centrivap system. The concentrations of the solutions were calculated from the weight of the solid residues.

Cell Growth and Western Blot (WB):

RCS, 293T and MCF7 cells were cultivated in DMEM (Sigma-Aldrich, St. Louis, Mo.) supplemented with 10% FBS and penicillin/streptomycin (Life Technologies, Carlsbad, Calif.). For growth assays, $2.5 \times 10^2$ RCS cells per well were seeded in 96-well plates and grown for 5 days. Cell numbers were determined by crystal violet staining as described in Krejci, P. et al.: Mammalian Cell-Based Assay for Identification of Inhibitors of the Erk MAP Kinase Pathway. *Invest. New Drugs* 2007, 25, 391-39. For WB, cells were extracted into Laemmli sample buffer (0.125 M Tris-Cl pH 6.8, 20% glycerol, 4% SDS, 0.005% bromophenol blue). Extracts were resolved by SDS-PAGE, transferred onto a PVDF membrane and visualized by chemiluminescence (Thermo Scientific, Rockford, Ill.). Media with FGF2 and/or ND were preincubated for 8 hours at 37° C. and 5% $CO_2$.

Figure 1:
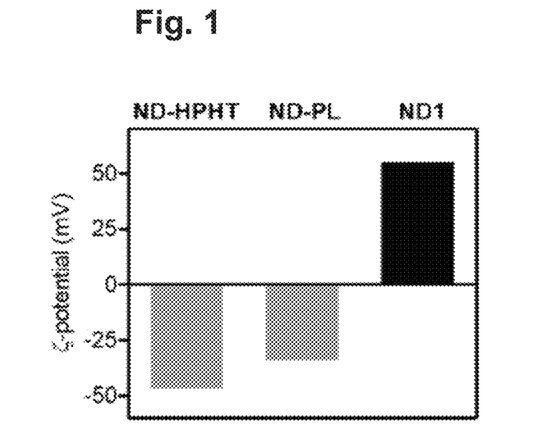
FIG. 1 The ξ-potentials of the ND particles used. ND-HPHT, high-pressure, high-temperature NDs; ND-PL and ND1, detonation NDs with negative and positive ξ-potentials, respectively.

Results:

For effective sequestration of FGF, the NDs must show positive ξ-potential. Three types of NDs were tested: detonation NDs with either positive or negative ξ-potentials (ND1 and ND-PL, respectively), and oxidized HPHT NDs with negative ξ-potential (FIG. 1). Rat chondrosarcoma (RCS) cells, which expressed the cell surface FGF-receptors FGFR2 and FGFR3, were used. RCS cells respond to the activation of FGFR signalling, via the addition of the prototypical FGF ligand FGF2, with a well-characterized array of phenotypic changes. These changes include potent growth arrest, loss of the extracellular matrix and the induction of premature senescence. RCS cells offer a particular advantage for inhibitor evaluation because only specific targeting of the FGF pathway can restore cell growth, and thus inhibitor interference with other, pro-growth pathways will not generate a positive response in the growth arrest assay.

Figure 2:
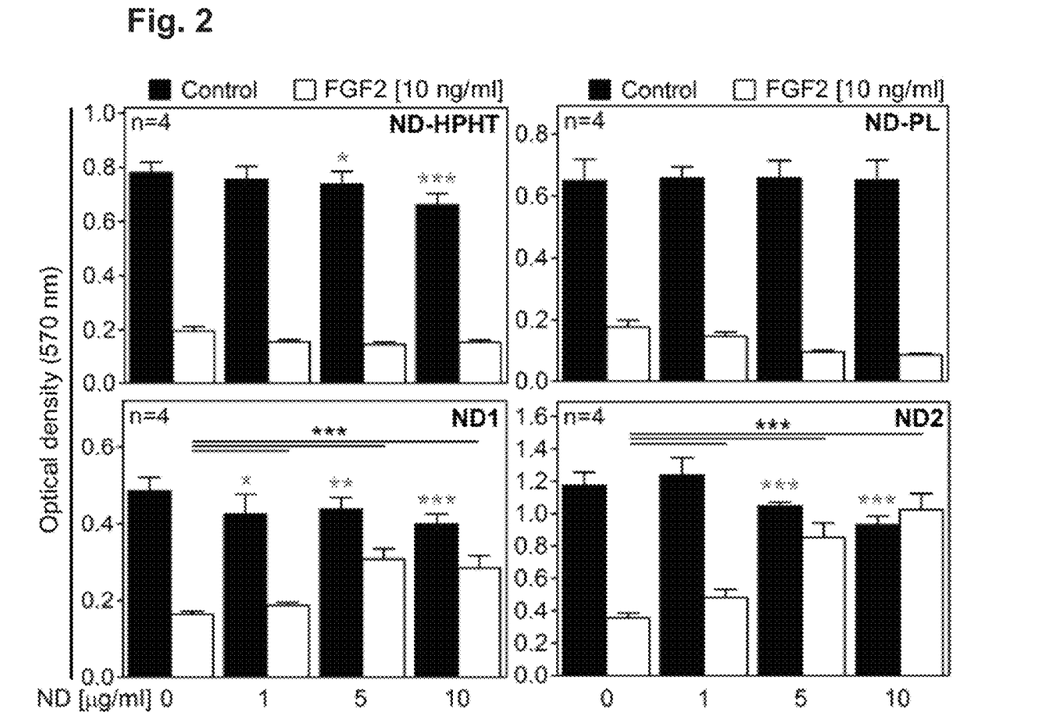
FIG. 2 NDs inhibit FGF2 signalling in cells. RCS cells were treated in medium containing 10% FBS with FGF2 and four types of NDs differing in ξ-potential and particle size for 72 hours; the FGF2-mediated growth arrest was quantified by crystal violet staining. Note the rescue of the growth arrest phenotype in cells treated with ND1 and ND2. Data represent averages of eight biological replicates with the indicated SD. The statistics on differences in growth of untreated cells versus cells treated with NDs only are marked by stars (*$p<0.05$, $p<0.01$, *$p<0.001$, Student's t-test). The results represent four (n) independent experiments.

While NDs with negative ξ-potential (ND-PL or ND-HPHT) did not show any influence on FGF2 signalling, ND1 and ND2, which have positive ξ-potential, effectively reversed the cell growth arrest in a concentration-dependent manner (FIG. 2). Thus, ND1 restored RCS growth specifically, i.e., without simultaneous interference with serum-borne pro-growth signalling pathways, such as PDGF (platelet-derived growth factor) and insulin signalling.

The FGF binding to the ND further depends to a certain extent on the ND particles size. We separated a fraction of smaller NDs from ND1, obtaining sample ND2 (hydrodynamic diameter 21 nm) with decreased size and a narrower size distribution of particles (FIG. 2). The rescue of FGF-mediated RCS growth arrest by ND2 was more effective than that by ND1. This result indicates that smaller size of ND particles causes higher activity.

Example 2

Figure 3:
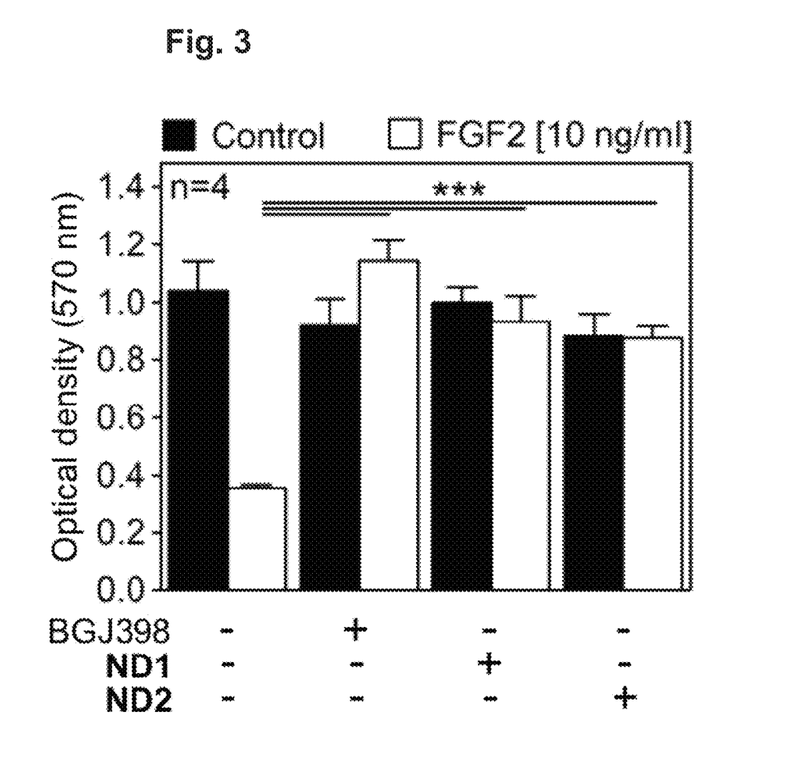
FIG. 3 The effect of ND1 and ND2 (10 μg/ml) on FGF2-mediated RCS growth arrest compared to a chemical inhibitor of FGFR kinase activity BGJ398 (10 nM).

To compare the efficacy of ND1 and ND2 with an established approach to the inhibition of FGF signalling, we performed the FGF2 growth arrest assay with a small-molecule inhibitor of FGFR catalytic activity, BGJ398 (Guagnano, V.; Furet, P.; Spanka, C.; Bordas, V.; Le Douget, M.; Stamm, C.; Brueggen, J.; Jensen, M. R.; Schnell, C.; Schmid, H.; et al. Discovery of 3-(2,6-Dichloro-3,5-Dimethoxy-Phenyl)-1-{6-[4-(4-Ethyl-Piperazin-1-Yl)-Phenylamino]-Pyrimidin-4-Yl}-1-Methyl-Urea (NVP-BGJ398), a Potent and Selective Inhibitor of the Fibroblast Growth Factor Receptor Family of Receptor Tyrosine Kinase. *J. Med. Chem.* 2011, 54, 7066-7083), which is currently being evaluated in clinical trials for FGFR-driven cancer (Tanner, Y.; Grose, R. P. Dysregulated FGF Signalling in Neoplastic Disorders. *Semin. Cell Dev. Biol.* 2016, 53, 126-135). BGJ398 rescued the FGF2-mediated growth arrest phenotype to a similar extent to that of ND1-2 (FIG. 3).

Example 3

For this experiment, ND1 were further purified by dialysis: ND1 colloidal solution (1 ml, 10 mg/ml) was dialysed 5× against water in 6-8 kDa dialysis tubing (Spectra/Por), filtered using a 0.2 μm PVDF syringe filter and diluted (9 ml, 1.0 mg/ml).

Figure 4A:
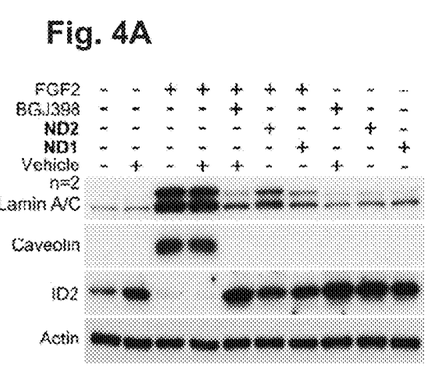

Similar to the growth arrest, the FGF2-mediated induction of premature senescence in RCS chondrocytes, manifested as the upregulation of the senescence markers lamin A/C and caveolin and the downregulation of ID2 (Krejci, P.; Prochazkova, J.; Smutny, J.; Chlebova, K.; Lin, P.; Aklian, A.; Bryja, V.; Kozubik, A.; Wilcox, W. R. FGFR3 Signaling Induces a Reversible Senescence Phenotype in Chondrocytes Similar to Oncogene-Induced Premature Senescence. *Bone* 2010, 47, 102-110), was rescued by both ND1 and ND2 (FIG. 4A).

Figure 4B:
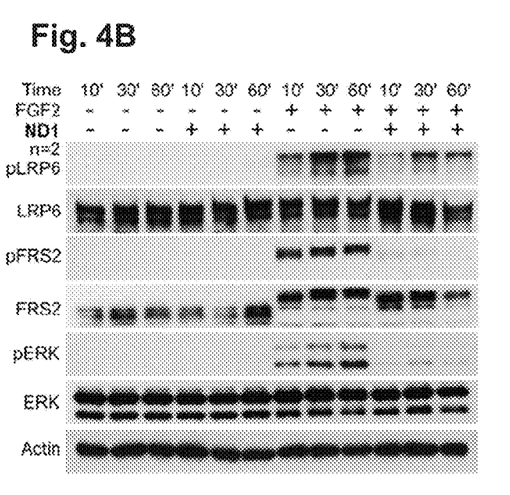

To gain further insight into the mechanisms of the ND-mediated inhibition of FGF signalling, the effect of ND on the activation of FGFR signal transduction in RCS cells was explored. Treatment with FGF2 induced potent phosphorylation of well-established mediators of FGF signalling, including ERK, the adapter protein FRS2 involved in ERK pathway activation, and the WNT pathway co-receptor LRP6, which is known to be phosphorylated by FGF signalling during its interaction with WNT/β-catenin signalling. FIG. 4B shows that the FGF2-mediated phosphorylation of ERK, FRS2 and LRP6 was inhibited by ND1. As activation of the ERK pathway mediates both growth arrest and premature senescence in RCS cells, the inhibition of ERK activation thus explains the ND-mediated rescue of the FGF2 phenotypes in these cells.

Figure 4C:
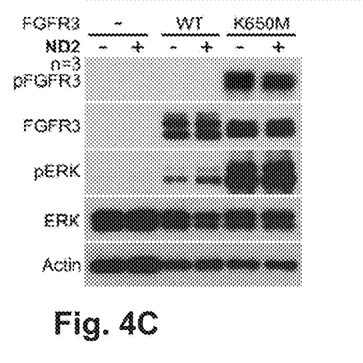

Our data show that NDs inhibit FGF signalling in cells by interaction with FGF2 ligand or with its receptors FGFR2 and FGFR3. Because FGFR3 overexpression in cells leads to its FGF ligand-independent dimerization and activation in cells, it was tested whether this process can be inhibited by NDs. Expression of wildtype FGFR3 or its activating, disease associated mutant K650M (Tavormina, P. L.; Bellus, G. A.; Webster, M. K.; Bamshad, M. J.; Fraley, A. E.; McIntosh, I.; Szabo, J.; Jiang, W.; Jabs, E. W.; Wilcox, W. R.; et al. A Novel Skeletal Dysplasia with Developmental Delay and Acanthosis Nigricans Is Caused by a Lys650Met Mutation in the Fibroblast Growth Factor Receptor 3 Gene. Am. *J. Hum. Genet.* 1999, 64, 722-731) in 293T cells lead to ligand-independent activation of FGFR3-ERK signalling, which was not inhibited by ND2 (FIG. 4C).

Altogether, it is demonstrated in Examples 1-3 that nanodiamond particles with positive ξ-potential (ND1, ND2), but not those with negative ξ-potential (ND-PL, ND-HPHT), effectively inhibit FGF signalling in cells via protein-nanoparticle interactions. Notably, all experiments were successfully performed in tissue culture medium containing 10% fetal bovine serum (containing approximately 6 mg/ml proteins), while the concentration of FGF was typically $6 \times 10^5$-fold lower (10 ng/ml; 0.61 nM for FGF2) and the NDs were extremely diluted (≤10 µg/ml, which corresponds approximately to ≤0.4 nM ND concentration). The exposure of inorganic nanoparticles and particularly of nanodiamonds to this protein-rich environment typically leads to the rapid formation of a strongly bound protein corona. Thus, the observed interference with FGF signalling had to be mediated by unusually strong protein-ND interactions to overcome the concomitant ND interactions with serum proteins.

Figure 5A:
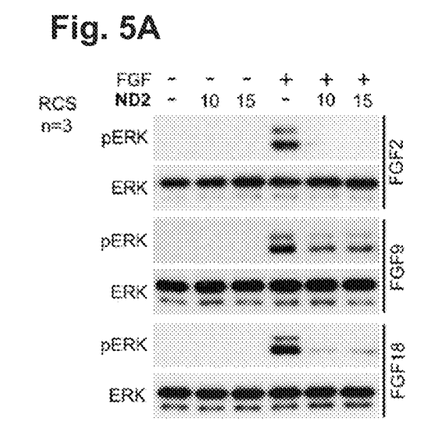
Figure 5B:
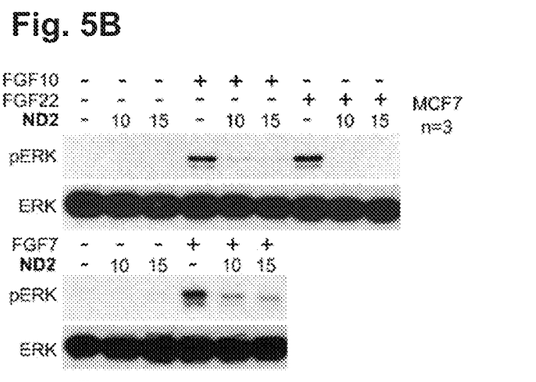

Example 4: NDs Inhibit Signalling of Multiple FGFs but not TGFβ1, IL6, IFNγ, EGF and NGF Having determined that NDs inhibit the activation of FGF signalling mediated by FGF2, it was confirmed that this effect is achieved for other ligands belonging to the FGF family Among the existing FGF ligands, FGF1/2/4/5/6/8/9/16/17/18 can activate ERK and cause growth arrest in RCS cells. However, only FGF2, FGF9 and FGF18 can achieve this effect alone, while all other FGFs require stabilization with heparin due to their low intrinsic stability. Because the addition of heparin could interfere with the ND-FGF interaction, in this test, the effect of NDs only on FGF9 and FGF18 was tested. Similar to FGF2, the activation of ERK mediated by treatment with FGF9 and FGF18 was rescued by ND2 (FIG. 5A). As shown before, RCS cells cannot respond to FGF ligands belonging to the FGF7 family (FGF7/10/22) due to the lack of the appropriate FGFR variants. Thus, human breast carcinoma MCF7 cells were used to test the effect of ND on FGF7/10/22 signalling. FIG. 5B demonstrates ERK activation mediated by FGF7, FGF10 and FGF22 treatment in MCF7 cells, which was rescued by ND2.

Figure 5C:
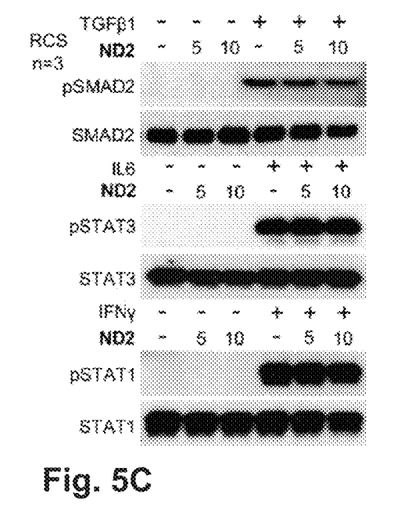
Figure 5D:
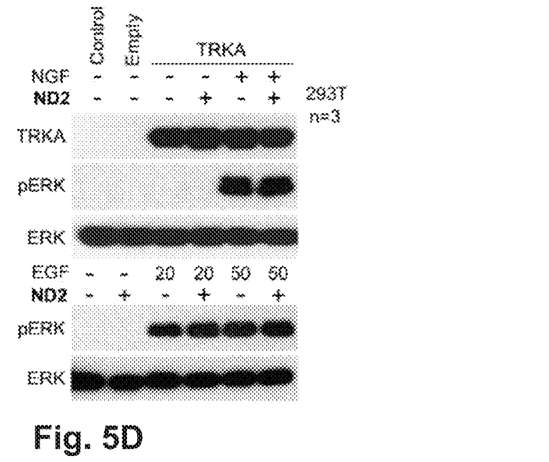
Figure 6A:
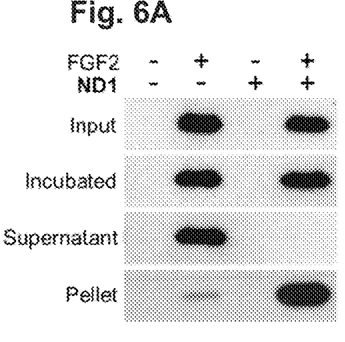
Figure 6B:
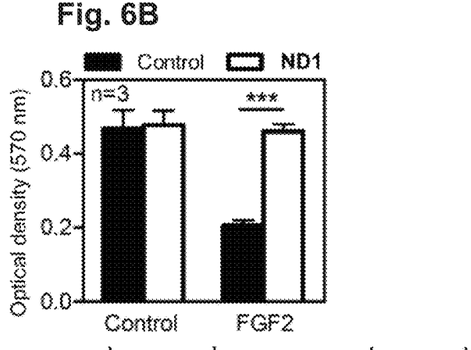
Figure 6C:
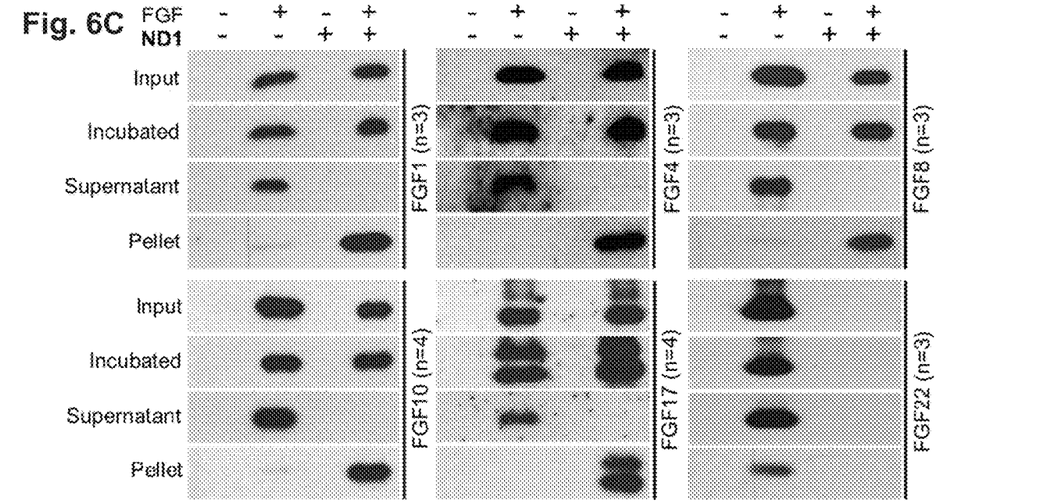
Figure 6D:
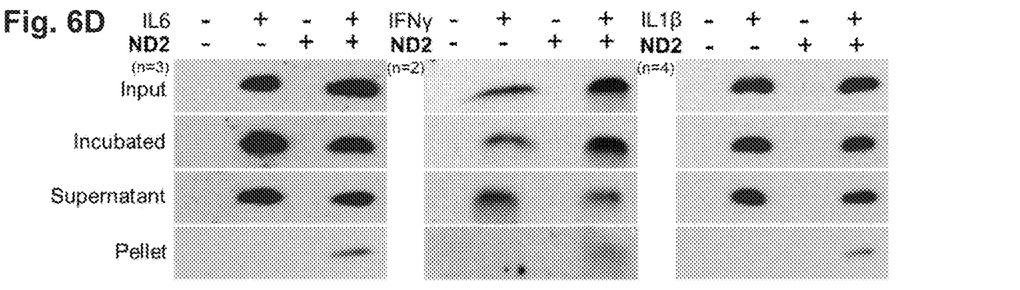

Furthermore it was confirmed that NDs do not inhibit other signalling systems unrelated to FGF. The tested systems were selected based on the diversity of their mechanisms of ligand-receptor interactions and on the diversity of their action in vivo. We thus determined the effect of ND on the signalling of a morphogene (TGFβ1), two unrelated cytokines (IL6, IFNγ), and two unrelated growth factors (EGF, NGF). In RCS cells, we found no effect of ND on the phosphorylation of SMAD2 transcriptional regulator in response to cell treatment with TGFβ1, on the phosphorylation of STAT3 transcriptional regulator in response to IL6 treatment, or on the phosphorylation of STAT1 in response to cell treatment with IFNγ (FIG. 5C). These data indicate that NDs do not interfere with TGFβ1, IL6 and IFNγ signalling. Similarly, in 293T cells, no effect of ND2 was observed on the activation of EGF signalling via cell treatment with EGF or on the activation of NGF signalling triggered by the NGF treatment of cells transiently expressing the NGF-receptor TRKA (FIG. 5D). Hence, no effect on other ligand-receptor systems than FGF was observed. The sequestration and binding is thus highly selective to FGF family Example 5: NDs Sequester Multiple FGF Ligands To document the sequestration of other members of FGF family by ND, various human recombinant FGFs were incubated with NDs in DMEM supplemented with 10% fetal bovine serum (FBS) for 8 hours, the NDs were collected by ultracentrifugation and analysed for the presence of FGF by western blotting with FGF-specific antibodies. First, an effective depletion of medium FGF2 after incubation with ND1 dialyzed in the same way as in Example 4 was found (FIG. 6A). Correspondingly, lack of growth arrest in RCS cells grown in the FGF2-depleted media was observed (FIG. 6B). Similar experiments carried out with other FGFs demonstrated an efficient ND-mediated depletion of recombinant FGF1, FGF 4, FGF8, FGF10, FGF17, and FGF22 (FIG. 6C). No significant ND-mediated depletion of the recombinant signalling proteins IL6 and IFNγ was found (FIG. 6D). Because interleukin 1β (IL1β) shares evolutionary origins with FGFs, we tested IL1β in the depletion studies as well. No ND-mediated depletion of IL113 was found (FIG. 6D), demonstrating that sequence context is more important than secondary structure in the FGF-ND interaction.

Example 6: NDs Inhibit FGFR Signalling in Mouse Limb Explant Cultures

Tibias obtained from E18 mouse embryos were grown for 8 days at 37° C. in DMEM supplemented with ND2 (100 µg/ml) and FGF2 (50 ng/ml), with daily media changes. The length of the tibias was measured at the beginning of the experiment (day 0) and at the end of cultivation (day 8) in Axio Vision (Zeiss, Germany). Animal experiments were reviewed and approved by the Institutional Animal Care and Use Committee at the Institute of Animal Physiology and Genetics AS CR (Libechov, Czech Republic; 213/2011).

The structural selectivity and tight binding of certain FGFs to NDs can be used as therapeutics for FGF-related diseases. To test the efficacy of NDs in intervening with FGF-related pathological processes in complex biological systems, we utilized an established model based on limb explants isolated from E18 mouse CD1 embryos (Gudernova, I.; Vesela, I.; Balek, L.; Buchtova, M.; Dosedelova, H.; Kunova, M.; Pivnicka, J.; Jelinkova, I.; Roubalova, L.; Kozubik, A.; et al. Multikinase Activity of Fibroblast Growth Factor Receptor (FGFR) Inhibitors SU5402, PD173074, AZD1480, AZD4547 and BGJ398 Compromises the Use of Small Chemicals Targeting FGFR Catalytic Activity for Therapy of Short-Stature Syndromes. *Hum. Mol. Genet.* 2016, 25, 9-23). When isolated from the embryos, the limb explants continue their growth programme for several days in culture, driven by the intrinsic signalling of several pathways such as TGF/BMP, WNT and hedgehog, which act in concert to ensure proper chondrocyte proliferation and differentiation. The limb explant model thus allows evaluation of the specificity and efficacy of the ND-mediated inhibition of FGF signalling in a complex tissue environment where many protein interactions must remain intact to allow normal growth. Similar to RCS chondrocytes, the activation of FGFR3 in limb explants inhibits their growth via impairing both proliferation and differentiation of the limb chondrocytes. This effect stems from the physiological role of FGFR3 as a negative regulator of skeletal growth.

Figure 7:
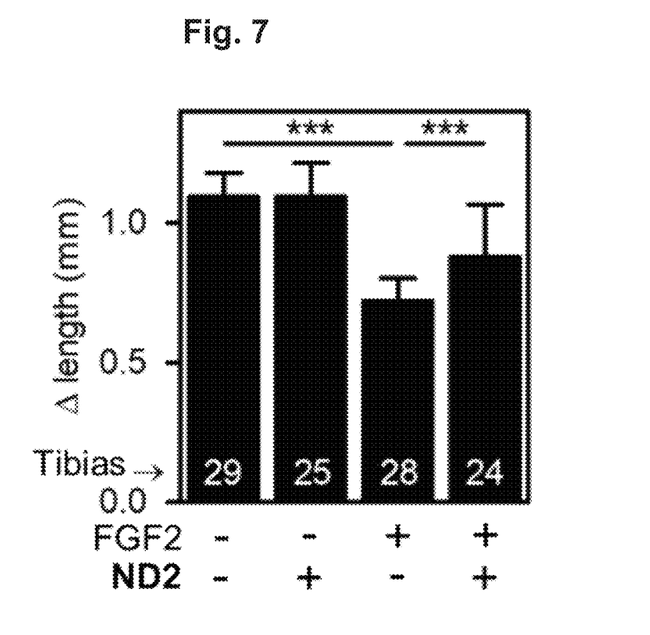
FIG. 7 NDs inhibit FGF signalling in limb explant cultures. Tibias isolated from E18 mice embryos were cultured in medium containing 10% FBS, 50 ng/ml of FGF2, and 100 μg/ml of ND2 for 8 days. The tibia length differences at isolation and after 8 days of incubation (A length) were determined and graphed. Statistically significant differences are highlighted (Student's t-test, ***$p<0.001$). The results are a compilation of six independent experiments; n, the number of tibias analysed.

Continuous treatment with FGF2 for 8 days resulted in significant inhibition of the limb explant growth accompanied by a reduction in hypertrophic cartilage. These effects were reversed by treatment with ND2 (0.1 mg/ml, 0.5 nM solution). NDs partially rescued the FGF2 growth-inhibitory effect, including restoration of the hypertrophic cartilage (FIG. 7). Normal growth and tissue microanatomy were found in limb explants cultured with ND2 alone for 8 days, suggesting minimal influence of the NDs on non-FGF-related signalling pathways regulating limb growth.

The invention claimed is:

1. A method of treatment of a disease caused by aberrant FGF-FGFR signaling and/or aberrant FGF-FGFR interaction, consisting of administration of nanodiamonds having a positive $\zeta$-potential of at least 1 mV to a subject in need of such treatment,
wherein the disease caused by the aberrant FGF-FGFR signaling and/or aberrant FGF-FGFR interaction is selected from developmental defects and metabolic disorders,
wherein metabolic disorders do not include cancer.

2. The method according to claim 1, wherein one or more FGF family members are sequestered by the administered nanodiamonds having a positive $\zeta$-potential of at least 1 mV.

3. The method according to claim 1, wherein the disease caused by the aberrant FGF-FGFR signalling and/or aberrant FGF-FGFR interaction is selected from craniosynostoses, skeletal dysplasias, dwarfism and impaired bone growth or regeneration.

4. The method according to claim 1, wherein the nanodiamonds have the positive $\zeta$-potential of at least 20 mV.

5. The method according to claim 1, wherein the nanodiamonds have an average diameter of primary particles in the range of 1 to 10 nm, as measured using transmission electron microscopy.

6. The method according to claim 1, wherein the nanodiamonds have a hydrodynamic diameter, determined as peak maximum size using dynamic light scattering, within the range of 1-100 nm.

7. The method according to claim 4, wherein the nanodiamonds have the positive $\zeta$-potential of at least 40 mV.

8. The method according to claim 6, wherein the nanodiamonds have a hydrodynamic diameter, determined as peak maximum size using dynamic light scattering, within the range of 1-70 nm.

9. The method according to claim 8, wherein the nanodiamonds have a hydrodynamic diameter, determined as peak maximum size using dynamic light scattering, within the range of 3-50 nm.

* * * * *